United States Patent [19]

Rosen

[11] Patent Number: 4,988,292
[45] Date of Patent: Jan. 29, 1991

[54] ABUTMENT FOR ORTHODONTIC ANCHORAGE TO A DENTAL IMPLANT FIXTURE

[76] Inventor: David B. Rosen, 9 Trodden Path, Lexington, Mass. 02173

[21] Appl. No.: 385,193

[22] Filed: Jul. 26, 1989

[51] Int. Cl.$^5$ .............................................. A61C 3/00
[52] U.S. Cl. ......................................... 433/8; 433/10; 433/17; 433/173
[58] Field of Search ................... 433/8, 9, 17, 23, 173, 433/174, 175, 176

[56] References Cited

U.S. PATENT DOCUMENTS

| | | | |
|---|---|---|---|
| 3,028,671 | 4/1962 | Berger | 433/8 |
| 3,127,677 | 4/1964 | Schechter | 433/17 |
| 3,452,436 | 7/1969 | DeWoskia | 433/23 |
| 4,024,638 | 5/1977 | Linkow et al. | 433/176 |
| 4,522,596 | 6/1985 | Ashkinazy | 433/173 |
| 4,738,062 | 4/1988 | Dickey | 433/173 X |
| 4,850,870 | 7/1989 | Lazzara et al. | 433/173 X |

FOREIGN PATENT DOCUMENTS 2425842  1/1980  France ..................... 433/8

OTHER PUBLICATIONS

"Dental Implants Used as Orthodontic Anchorage", J. B. Douglass and D. M. Killiany, J. Oral Implantology 13, No. 1, pp. 28, 32, 1987.
"Use of Endosteal Implants as Orthodontic Anchorage", Kraut, R. A, 1988, Hammer, H. S. and Wheeler, J. J., Compendium of Continuing Education in Dentistry 9, No: 10, pp. 796–801.
"Use of Implants in Orthodontics", P. A. Shapiro and V. G. Kovick, Dental Clinics of North America 52 No. 3, pp. 539–550, Jul. 1988.

Primary Examiner—Robert P. Swiatek
Assistant Examiner—Nicholas D. Lucchesu
Attorney, Agent, or Firm—Alfred H. Rosen

[57] ABSTRACT

An abutment for orthodontic anchorage is mountable on an osseointegrated dental implant fixture in the same manner as components used to support prosthodontic restorations. This abutment is adjustable around the axis of the implant fixture, and it supports a mount for holding an orthodontic anchor fixed to a buccal or a lingual side of the abutment. The mount is adjustable around an axis running between the buccal and lingual surfaces.

16 Claims, 2 Drawing Sheets

ABUTMENT FOR ORTHODONTIC ANCHORAGE TO A DENTAL IMPLANT FIXTURE

INTRODUCTION

This invention relates in general to the dental field of orthodontics, and more particularly to an abutment for orthodontic anchorage to a dental implant fixture in a patient who is endentulous at the site where such anchorage is desired.

BACKGROUND OF THE INVENTION

In one class of systems used in orthodontic practice arch-wires cooperating with brackets affixed to buccal surfaces of teeth are used to adjust the relative positions of teeth in a dental arch with appropriate forces applied over time to individual teeth in the arch. These wires are anchored at their ends to tubes, hooks, and the like affixed to the patient's molars, or other suitable teeth. Elastics and ligature threads are also in orthodontic use and these, too, cooperate with traction hooks and buttons affixed to surfaces of a patient's molars, or other suitable teeth.

In cases of patients who have lost their molars, or otherwise lack suitable anchorage, the use of molar tubes, hooks, buttons and the like has not been available to orthodontists. However, now that the art of dental implantology is developed to provide a variety of artificial root fixtures, notably the endosseous implant fixture, an opportunity exists to fill that need for partially edentulous patients.

It has only recently been ascertained that an endosseous dental implant can be used to enhance dental anchorage in orthodontics. A report by Douglass, J. B. and Killiany, D. M. entitled "Dental Implants used as Orthodontic Anchorage" J. Oral Implantology 13 No. 1 pp. 28–32, 1987 describes experiments with rats using implanted posts extending 3 mm. coronally to which ligature wire was tied. A later article by Kraut, R. A., Hammer, H. S. and Wheeler, J. J., entitled "Use of Endosteal Implants and Orthodontic Anchorage" Compendium of Continuing Education in Dentistry 9 No. 10 pp. 796–801, 1988 reports several cases in which endosteal implants were used as orthodontic anchors in humans. In each case cast crown forms were fabricated to accept orthodontic molar bands, and those crowns were affixed to the implants.

GENERAL NATURE OF THE INVENTION

A dental implant fixture in the class of endosseous implants consists essentially of an elongated body implanted in the patient's jawbone and having a socket for receiving a fitting or fittings which fix a prosthodontic restoration on the implanted fixture. Commonly, the socket is an internally-threaded receiving bore, and the restoration is fixed to the implanted fixture with a bolt threaded into that bore. Other forms of dental implants are in use, and a wide variety of materials are used in making them. This invention is disclosed in connection with the endosseous implant fixture as currently known to be in use, as a best mode now known to practice the invention. It will be understood that the invention is not limited to the details of the illustrative disclosure; to the contrary, the invention is intended for use with any and all substitutes for natural tooth structures that are capable of providing the required anchorage, whether presently known or made available in the future.

The present invention teaches a new way to use dental implants for orthodontic anchorage. Generally according to the invention an abutment, designed and intended as a component for use with dental implant systems, is fabricated to provide orthodontic anchorage for archwires, ligatures and elastics. The invention provides, in one of its preferred forms, an abutment for orthodontic anchorage which comprises a tubular body having at a first end an internal flange providing a shoulder for the head of a bolt by which to attach the body to an endosseous implant fixture of the type having an internally-threaded receiving bore. Exteriorly, the first end of the tubular body is shaped to mate with the gingival end of the implant fixture in the same manner as components that are in use with that fixture for prosthodontic restoration purposes. Between the flange and the second end of the tubular body, the side walls of the body are apertured at diametrically-opposite locations, providing two similar holes for the passage of the support means of a molar tube or other anchoring device diametrically across the tubular body, clear of the head of the bolt when the latter is in place on the shoulder. Such support means can take the shape of a mounting shaft in the form of an internally-threaded pipe fixed at one end to the orthodontic anchoring device and fitted through one of the holes in the tubular body with its other end extending toward the other hole. A retaining screw passing through the second hole threadedly engages in the pipe, and is turned into the pipe to draw the orthodontic anchoring device firmly against the opposite side of the tubular body. The invention allows the anchoring device, e.g.: a molar tube, to be positioned rotationally around the axis of the pipe, and at the same time it allows the tubular body to be positioned rotationally around the axis of the socket or receiving bore in the implant fixture.

Thus the orthodontist can adjust a molar tube in two orthogonally-related planes, to bring the molar tube into a desired position relative to the end of an archwire that is to be anchored in the molar tube.

GENERAL DESCRIPTION OF THE DRAWINGS

The invention is disclosed in fuller detail with reference to the accompanying drawings, in which.

Figure 1A:
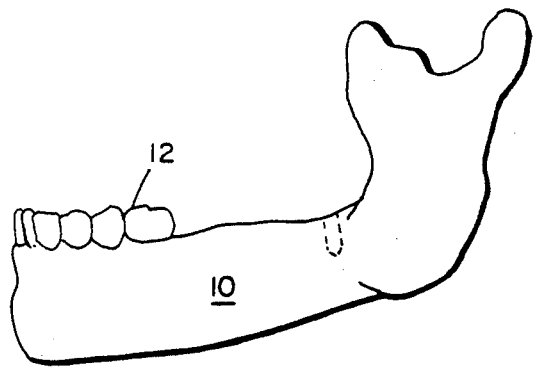
FIG. 1 (A&B) illustrates the problem to which the invention is particularly addressed.
Figure 1B:
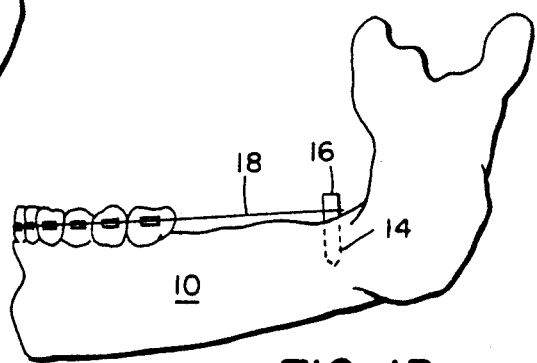

As appears in FIG. 1A, the patient whose lower jaw 10 is illustrated has lost all of the molars in the left-hand side of the lower arch. An attempt to straighten this patient's anterior teeth using an archwire (not shown) anchored to a molar via a molar tube or the like cannot be made. FIG. 1B shows how the present invention fills this need. An endosseous implant fixture 14 fixed in the lower jaw 10 at the site of a missing molar is used to support an abutment for orthodontic anchorage 16, and an archwire 18 is anchored to it at one end. The abutment 16 is illustrated in FIGS. 2 to 5, inclusive.

Figures 2, 5:
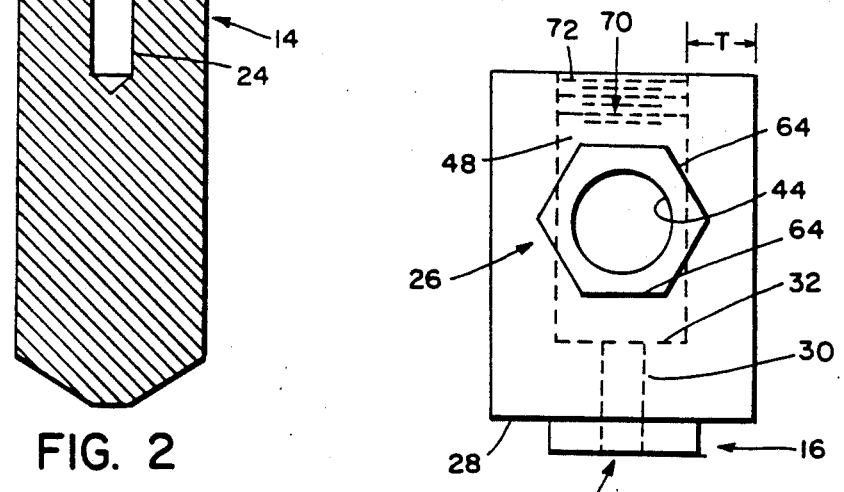
FIG. 2 is a partially-exploded side view of the invention.
FIG. 5 is a buccal view of FIG. 4.
Figure 4:
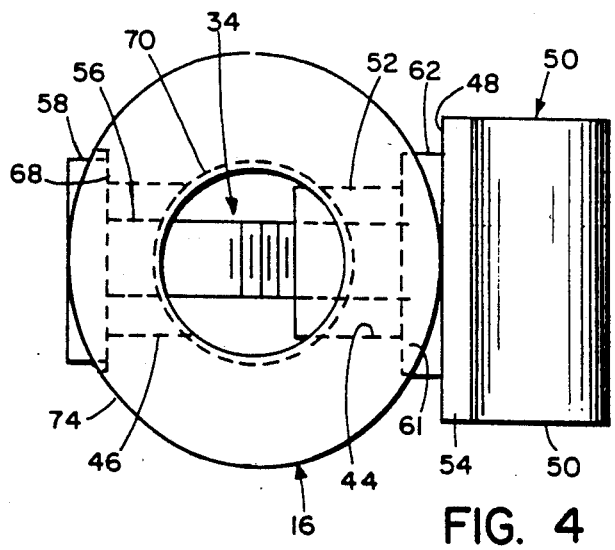
FIG. 4 is an occlusal view of FIG. 3.

In FIG. 2, the implant fixture 14 is shown having an internally-threaded receiving bore 24. The abutment 16 of the invention that is illustrated consists primarily of a tubular body 26 having at a first end, the lower end 28 as shown in the drawing, an internal flange 30 providing a shoulder 32 for the head 34 of a bolt 36 by which to attach the abutment 16 to the implant fixture 14. In order to prevent rotation of the abutment 16 relative to the implant fixture 14, around the axis of the receiving bore 24, the gingival end 22 of the implant fixture and the first end 28 of the abutment 16 may be provided with interlocking male and female anti-rotation fittings 40,42, respectively. As shown, these are a hexagonal socket 42 and a hexagonal projection 40, but they may be reversed, and they may be changed in shape, as desired. A molar tube 50 is fixed to a side surface of the abutment 16.

Figure 3:
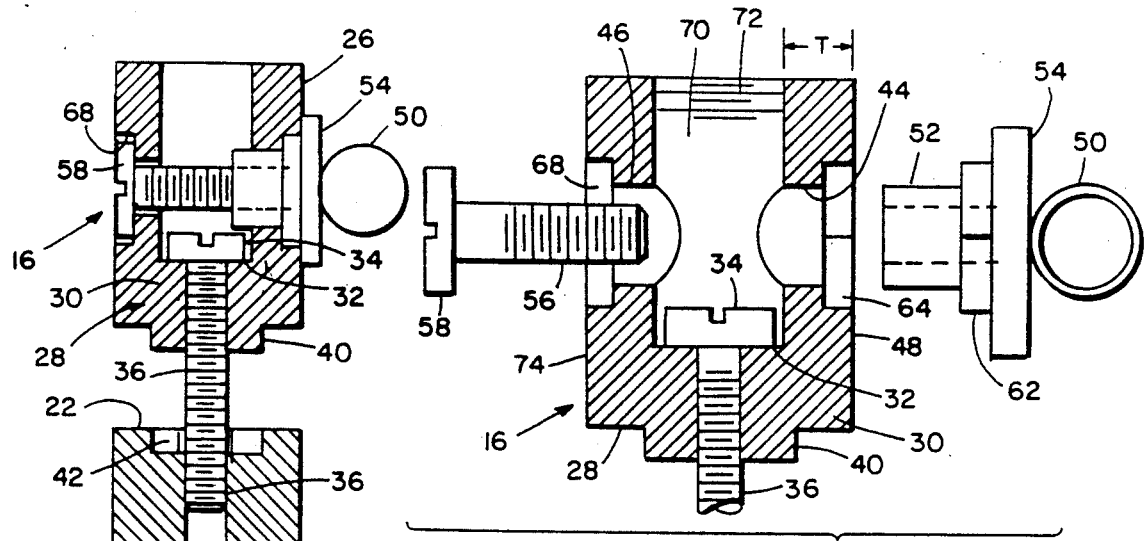
FIG. 3 is an expanded side view of the abutment shown in FIG. 2.

Referring now to FIG. 3, the molar tube 50 is fixed via a mounting flange 54 to one end of a mounting shaft in the form of a pipe 52 which is internally threaded. The length of this pipe is less that the diametric distance across the tubular body 26, as seen in FIG. 3, but preferably more that the thickness "T" of the wall of the tubular body. The flange 54 to which the molar tube is mounted intervenes between the pipe and the molar tube. A machine screw 56 having a head 58 has threads which mate with the internal threads in the pipe 52. The tubular body 26 has two diametrically-opposed holes 44,46. The pipe 52 passes through a first hole 44 and the screw 56 passes through the second hole 46 to engage in the pipe. The screw is turned in the pipe until the flange 54 comes to rest against the adjacent sidewall 48 of the abutment 16. By loosening the screw 56 in the pipe 52, but not necessarily removing the screw from the pipe, the molar tube 50 can be adjusted around the axis of the pipe. In order to lock the molar tube in position, against the possibility that the screw 56 may loosen a small amount after the patient leaves the orthodontist, the flange 54 and the adjacent sidewall 48 may be provided with interlocking male and female anti-rotation fittings 62,64, respectively, similar to the anti-rotation fittings 40,42, and subject to the same freedoms of interchangeability and variations in design. The screw 56 and the pipe 52 are preferably long enough that the screw can be loosened to release the anti-rotation fittings 62,64 to allow the molar tube 50 to be adjusted rotationally around the axis of the pipe without having to remove the screw entirely from the pipe.

In use of the invention as illustrated, the surface 48 of the abutment 16 is the buccal surface and the opposite surface 74 is the lingual surface. The outer shape of the abutment need not be round. The abutment may be contoured in cross-section to approximate the shape of a molar, so that the buccal surface 48 may be wide and flat, rather than arcuate. If the buccal surface is so contoured, it will present a relatively flat surface to the flange 54. The female anti-rotation fitting 64 is shown in FIG. 5, as is the hole 44 in the buccal surface 48 through which the pipe 52 passes.

The abutment 16 can be used to support a wide variety of fittings and attachments of use to orthodontists. Examples are hooks, and combined molar tubes and hooks. The abutment may also be used to support lingual attachments, such as lingual buttons, in which case the abutment may be rotated 180 degrees on the implant fixture 14, or the screw 56 and the fitting may be interchanged relative to the abutment without removing the abutment from the implant fixture. In the latter instance, each side of the abutment tube 26 may be provided with an anti-rotation fitting (e.g.: female fitting 64), and the head 58 of the screw 56 may be smaller in diameter than the anti-rotation fitting. To this end the recess 68 shown in FIGS. 2 and 3 for the head 58 may be a female anti-rotation fitting identical to the fitting 64 in the buccal surface 48.

The abutment 16 is intended to be compatible with, and capable of being an integral part of, a dental restoration plan for a patient who is molar-edentulous, and who may intend to acquire a full-mouth restoration. To this end the abutment is designed and intended to be useful with a dental implant fixture that may ultimately be used to support a prosthodontic restoration of the lost molars.

In the embodiment of the invention that is illustrated the molar tube 50 can be adjusted rotationally around the axis of the pipe 52, and the abutment 16 can be adjusted rotationally around the axis of the receiving bore 24, each independent of the other. The invention is applicable to all structures in which one or both of these independent adjustments is or are possible.

For convenience in closing the opening into the tubular body 26, the occlusal end of the opening 70 may be internally threaded, as at 72 in FIG. 3, to receive a cap screw (not shown).

Figure 6A:
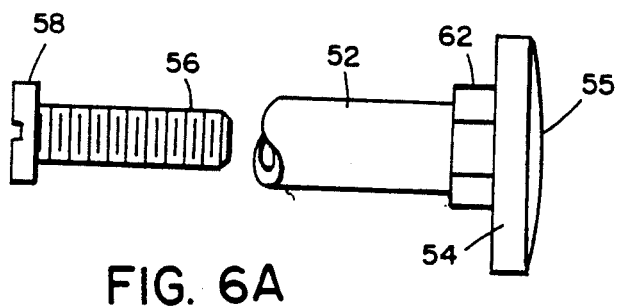
FIG. 6 (A&B) is a side view of a modification of the invention.
Figure 6B:
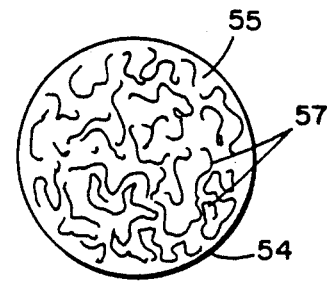
Figure 7A:
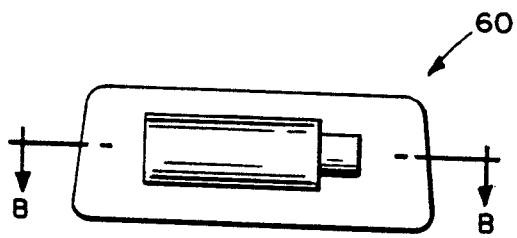
FIG. 7 (A&B) illustrates an orthodontic tube.
Figure 7B:
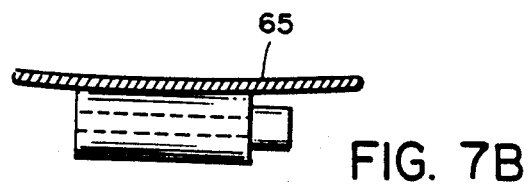

FIG. 6 illustrates a modification of the invention that allows the orthodontist to fix a bracket or an anchoring device (not shown) of his or her own choice to the abutment 16. In FIG. 6 the pipe 52 and the mounting flange 54 are shown as a unit, the face 55 of the flange being available to receive a bracket or an anchoring device. To this end the face 55 may be roughened, as is indicated at 57, to accept a cementitious or other bonding material of the kind normally used by orthodontists to affix brackets, tubes, traction hooks, buttons and the like to patients' teeth. The material providing the face 55 may be any material to which such bonding material will adhere substantially as it adheres to patients' natural teeth. Plastics materials such as a dental acrylic are suitable. The face 55 may be shaped to conform with the shape of the meeting surface of the anchoring device; for example, the meeting surface 65 of a molar tube 60 shown in FIG. 7, is generally rectangular and slightly concave in its longer dimension, so that the face 55 may be large enough to accommodate the longer dimension of the meeting surface and convex (as is indicated in FIG. 6) to accommodate the concavity of the meeting surface 65. The unit comprised of the pipe 52 and the mounting flange 54 may be made entirely of one material (e.g.: a plastics material), or as an alternative a separate material providing the face 55 may be attached to a unit 52,54 that is made of another material (e.g.: stainless steel) to which the available orthodontic bonding materials may not readily adhere. The unit 52,54 desirably includes the anti-rotation fitting 62. The retaining screw 56 and its head 58 may be made of the same material as the pipe 52.

In use of the FIG. 6 embodiment of the invention, the abutment 16 is installed in the patient's mouth, the orthodontist affixes a chosen orthodontic device (not shown) to the face 55 of the flange 54, and the pipe 52 and its retaining screw 56 are fitted to the abutment body 26, and adjusted to locate the attached orthodontic device in the desire position. With this embodiment of the invention the orthodontist can perform all cementing procedures outside the patient's mouth, and can easily change from one orthodontic device to another.

I claim:

1. For sue to benefit a patient who is endentulous at a site where orthodontic anchorage is desired, the combination of support means for an orthodontic anchoring device and an abutment for orthodontic anchorage to a dental implant fixture located at said site comprising an abutment body having at one end means to affix said body to said implant fixture, and means rotational around an axis which traverses said body intermediate its ends to affix said support means to an external surface of said body.

2. The combination according to claim 1 wherein the abutment body has buccal and lingual surfaces and said axis extends between said surfaces and, adjustable support means for holding an orthodontic anchoring device, when present, against one of said surfaces, said support means including means to adjust said device around said axis.

3. The combination according to claim 1 in which said body is generally tubular in shape having at said one end an internal flange providing a shoulder for a fastening device by which to affix said body to said implant fixture.

4. The combination according to claim 3 including means at said one end to cooperate with said implant fixture to adjustably fix the rotational position of said body relative to said implant fixture around the axis of elongation of said abutment.

5. A combination according to claim 3 in which said abutment body has first and second apertures diametrically opposite each other in its sidewalls providing a passage spaced from said flange across said body, said means to affix said support means comprises a shaft fitted in said passage and includes a mount for an orthodontic anchoring device, said mount being attached to one end of said shaft, and means which engages the other end of said shaft for tightening said mount to said external surface.

6. The combination according to claim 5 including an orthodontic anchoring device affixed to said mount.

7. The combination according to claim 5 in which said apertures are round and said shaft is rotatable in said passage across said abutment body.

8. The combination according to claim 7 including means cooperative between said mount and said external surface to prevent rotation of said mount relative to said body around the axis of rotation of said shaft in said passage.

9. A combination according to claim 1 in which said abutment body has aperture means intermediate its ends providing a passage across said body, said support means comprises a shaft fitted in said passage and includes a mount for an orthodontic anchoring device, said mount being attached to one end of said shaft, and means which engages the other end of said shaft for tightening said mount to said external surface.

10. The combination according to claim 9 including an orthodontic anchoring device affixed to said mount.

11. The combination according to claim 9 in which said passage across said abutment body is substantially round in cross section, and said shaft is rotatably fitted in said passage.

12. The combination according to claim 7 including means cooperating between said mount and said external surface to prevent rotation of said mount relative to said body around the axis of rotation of said shaft in said passage.

13. The combination according to claim 9 in which said shaft and said mount are a single unit made of a plastics material.

14. The combination according to claim 9 in which said shaft is a section of internally-threaded pipe and said means for tightening is a screw threadedly engaged in said other end of said shaft.

15. The combination according to claim 9 in which said mount has a surface adapted to bond with an adhesive used to affix orthodontic anchoring devices to natural teeth.

16. The combination according to claim 1 including an orthodontic anchoring device held to said external surface by said support means.

* * * * *